United States Patent [19]

Lee

[11] Patent Number: 5,498,720

[45] Date of Patent: Mar. 12, 1996

[54] CERTAIN TRIAZOLE COMPOUNDS AND THEIR PHARMACEUTICAL USES

[76] Inventor: An-rong Lee, 24, Alley 5, Lane 24, Sec.3, Tin-Chou Rd., Taipei, Taiwan

[21] Appl. No.: 112,716

[22] Filed: Aug. 26, 1993

[51] Int. Cl.[6] .................... C07D 401/04; C07D 403/04
[52] U.S. Cl. .................... 546/276; 548/247; 548/264.4
[58] Field of Search ................. 548/264.4, 247; 546/278, 275, 276

[56] References Cited

PUBLICATIONS

Sung et al., Journal of Heterocyclic Chemistry, vol. 29, No. 5, pp.–1101–1109 (Aug.–Sep. 1992).

*Primary Examiner*—Alan L. Rotman
*Attorney, Agent, or Firm*—W. Wayne Liauh

[57] ABSTRACT

In the invention of novel nonsteroidal antiinflammatory compounds the title novel triazole compounds, were synthesized from carboxylic acids, 2,5-acetonylacetone, or isoniazid, respectively. To give 4H-1,2,4-triazol-3-thiols. Treatment of 4H-1,2,4-tri-azol-3-thiols with methyl chloroacetate or methyl α-chloropropionate resulted in the formation of compounds I–VI. The antiinflammatory activity of those new triazole compounds were determined by the carrageenin-induced edema method and they showed potent activity. In the dosage form studies those compounds of formula I–VI were added suituble vehicleo to prepare antiinflammatory agents.

3 Claims, 2 Drawing Sheets

CERTAIN TRIAZOLE COMPOUNDS AND THEIR PHARMACEUTICAL USES

DESCRIPTION OF THE INVENTIONS

Background Art

In the past two decades, inspired by the success of indomethacin and ibuprofen, studies of new nonsteroidal antiinflammatory compounds were focused on the type of arylalkanoic acid and arylcarboxylic acid. The mechanism of antiinflammatory agents have not been establihed, even there has been existed potent anfiinflammatory agents in clinic such as e.g. isoxicam and piroxicam.

In 1976, Reid et al, treated acid hydrazides with carbon disulfide and refluxed under the basic conditions and gave crude 3-acyldithiocarbazates. The reaction of the crude 3-acyldithiocarbazates with hydrazinc hydrate produced 4-amino-4H-1,2,4-triazol-3-thiols, shown in FIG. 1 (J. Heterocyclic Chem., 1976, 13, 925).

In 1984, Maxwell et al, esterified the carboxylic acids then converted the resultant esters to acid hydrazides by treatment with hydrazine hydrate. The reaction of the acid hydrazides with suitable isothiocyanates gave thiosemicarbazides. Condensation and cyclization of thiosemicarbazides by reflexing with an aqueous sodium hydroxide solution gave 4H-1,2,4-triazol-3-thiols (J. Med. Chem., 1984, 27, 1565).

In the invention of novel compounds of formula I-VI shown in FIG. 2 wherein $R_1$ signify a 3-isoxazolo group, benzen, pyridine, or signify a benzene group which is optionally substituted by one or more halogens, or methoxyl group, or $C_{1-4}$ alkyl, or signify a pyridin group which is optionally substituted by one or more halogens, or methoxyl group, or $C_{1-4}$ alkyl, or signify a 3-isoxazole group which is optionally substituted by one or more halogens, or methoxyl group, or $C_{1-4}$ alkyl; and $R_2$ signify $C_{1-4}$ alkyl group, benzene, amine, or signify a benzene group which is optionally substituted by one or more halogens, or methoxyl group, or $C_{1-4}$ alkyl; and $R_4$; $R_5$, $R_6$ signify a hydrogen or $C_{1-}$alkyl group; $R_3$ signify a hydrogen. In the invention of novel nonsteroidal antiinflammatory compounds most of the starting materials were carboxylic acids, the others were isoniazid, or 2,5-acetonylacetone Those carboxylic acids were benzoic acid, pyridine, or, halobenzoic acid, methoxybenzoic acid, or the benzene ring of bengoric acid substituted by one or more halogen, or methoxyl group, or $C_{1-4}$ alkyl group, or the isoxazole of isoxazole carboxylic acids whih may be substituted by one or more halogens, or methoxyl group, or $C_{1-4}$ alkyl group.

The synthetic methods of 5-methyl-3-isoxazole carboxylic acids, were described in U.S. Pat. No. 2,908,688 (1959), which were prepared by reflexing 2,5-acetonylacetone with con. nitric acid. We found that the patent yields were much lower than our modified methods, and they were acsily overheated under the stated conditions.

In the invention of triazol compounds esterification of the starting materials of carboxylic acids with $C_{1-4}$ alkyl alcohol gave esters. In which, the acids were isoxazole carboxylic acids, benzoic acid, pyridine, or benzene ring of the benzoic acid, substituted by one or more halogens, or one or more methoxyl groups, or $C_{1-4}$ alkyl group, or isoxazole group substituted by one or more halogens, or methoxyl group, or $C_{1-4}$ alkyl group.

The esters were converted to acid hydrazides as formula V by treatment with hydrazine hydrate. The reaction of the acid hydrazides with suitable isothiocyanates gave 1-acyl-4-substituted-thiosemicarbazides as formula VI, or with carbon disuifide gave potasium 3-acyldithiocarbazates. As described above the formula VI were $C_{1-4}$ alkyl isothiocyanates, phenyl isothiocyanate, amino isothiocyanate, or benzene ring on the phenyl isethiocyanate is optionally substituted by one or more halogens, or methoxyl group, or $C_{1-4}$ alkyl group. Condensation and cyclization of formula VI by reflexing with an aqueous sodium hydroxide solution gave 4,5-disubstituted-4H-1,2,4-triazol-3-thiols. Condensation and cyclization of potassium 3-acyldithiocarbazates as described above gave 4-amino-5-substituted-4H-1,2,4-triazol-3-thiols. The 4-amino-5-substituted-4H-1,2,4-triazol-3-thiols and 4,5-disubstituted-4H-1,2,4-triazol-3-thiols are shown as formula I. The suitable isothiocyanates were ethyl or phenyl isothiocyanate.

Treatment of the formula I with formula VII in the presence of anhydrous potassium carbonate resulted in the formation of formula II. Hydrolysis of the formula II with an aqueous sodium hydroxide solution gave compounds of formula II, where $R_5$ group of formula II signify a hydrogen. The formula VII wherein $R_4$, $R_5$ signify a hydrogen, or $C_{1-4}$ alkyl group, preferably methyl chloroacetate, methyl α-chloropropionate.

Treatment of 4-amino-5-substituted-4H-1, 2, 4-tria-zol-3-thiols with formula VIII in refluxing ethanol gave the fused ring products of formula IV. However, 4-amino-5-substituted-4H-1,2,4-tria-zol-3-thiols were treated with one equivalent of ethanolic patessium hydroxide solution at room temperature followed by formula VIII and gave products formula III, which had no fused ring. The formula VIII wherein $R_6$ signify a hydrogen, or $C_{1-4}$ alkyl group; X signify a halogen group, preferably ethyl 4-chloroacetoacetate.

Those compounds in the invention of novel compounds of formula I-VI described as above were analyzed for their carbon, hydrogen and nitrogen content. Melting points were measured in open capillary tubes with an electrothermometer. Infrared spectra were recorded on a parkin-Elmer model 983G spectrometer. The $^1H$ NMR spectra were obtained on a Jeol FX-100 NMR spectrometer. Mass spectra were measured with a Jeol JMS-400 mass spectrometer.

The resulting free compounds of formula I–VI, including their inner salts of formula I–VI, can be converted into base salts by partial or complete neutralization with bases. Acid-added salts can also be converted into the corresponding free compounds of inner salts thereof in analogous manner.

The present invention likewise relates to the use of the compounds of formula I—VI and their salts, preferably for antipyretic, analgesic and antiinflammatory uses. Those antiinflammatory compounds were tested in sprague Dawely rats according to the method reported by Maxwell, et el. The invented compounds of formula I–VI were orally administered at a dose of 32 mg/kg to evaluate their ability for providing protection against edema induced by administration of 0.05 ml of a 1% suspension of carrageenin in 0.9% saline in hind paws of rats, using phenylbutazone and dexamethasone as references. The pharmacological data are shown in Table VII.

The pharmaceutical preparations according to the invention which contains compounds of the formula I–VI or pharmaceutically acceptable salts thereof are those for enteral or parenteral administration which contain the pharmaceutically active ingredient by itself or together with a pharmaceutically acceptable carrier material.

Suitable carriers for enteral user are, in particular, fillers, suchs as sugars, for example lactose, sucrose, mannitol, and binders, such as starch mucilage using, for example, wheat, rice or potato starch, and/or, if desired, distegrating or adjuncts. Those carriers for parenteral administration are, in particular, aqueous solutions and furthermore lipophilic solvents or vehicles, such as fatty oils, and/or, if desired, viscosity-increasing substance, for example, sodium carboxymethylcellulose, sorbitol. The preferred individual dosage is 50 to 300 mg for oral administration and 2 to 15 mg for intravenous administration and can be administered up to 3 times daily.

EXAMPLE 1: 5-Methyl-3-isoxazole carboxylic acid 3.94 ml (33.5 mmol) of 2 5-acetonylacetone, 20 ml of con. nitric acid in 25 ml of water were carefully mixed and then refluxed for 1 hr. After cooling to 0° C. a precipitate formed. The precipitate was isolated by filtration and purified by recrystallization from water to obtain the pure 31.3 g 5-methyl-3-isoxazole carboxylic acid.mp 175°–176° C.

EXAMPLE 2: Benzoylhydrazine 0.20 mol of benzoic acid was mixed with 260 ml of ethanol, and 30 ml of con. sulfuric acid was added. The reaction mixture was reacted completely and crystallized from ether. Ethyl benzoate was obtained (71.1%).

0.10 mol of ethyl benzoate obtained as above was heated under reflux with 2.5 equivalent of hydrazine hydrate and 30 ml of ethanol. after cooling to 0° C. a precipitate formed and crystallized from ethanol. Yield was 90.5%.

EXAMPLE 3: 4-[5-Methyl-3-isoxazolyl]-5-benzyl-4H-1,2,4-triazolethiol (1)

30.0 mmol of 5-methyl-3-isoxazole carboxylic acid was mixed with 1.2 equivalent of phenyl isothiocyanate and 30 ml of ethanol. The mixture was heated completely under reflux and crystallized from ether. 1-[5-Methyl-3-isoxazolyl]-4-benzyl-isothiocyanate was obtained. Yield was 71.1%.

25.0 mol of 1-[5-methyl-3-isoxazolyl]-4-benzyl-isothiocyanate obtained as above was heated under reflux with 30 ml of an aqueous sodium hydroxide solution. The precipitate was isolated by filtration and purified by recrystallization from ethyl acetoacetate to obtain the pure 4-[5-methyl-3-isoxazolyl]-5-benzyl -4H-1,2,4-triazolethiol. Yield was 94.2%.

EXAMPLE 4: 4-amino-5-pyridyl-4H-1,2,4-triazolethiol (9)

Potassium hydroxide (0.15 mole) in 100 ml of absolute alcohol and 0.10 mol of Isoniazid were mixed together until the solution became clear. To the solution was added 0.15 mol of carbon disuifide and stirred at 25° C. for 3 hr and then 100 ml of ethyl ether was added to form a precipitate. The precipitate of potassium 3-lsonicotinyidithiocarbazate was filtered and washed with ethyl ether for several times, then mixed with 160 mmol of hydrazine hydrate and 2 ml of water. The solution was refluxed for 1 hr. After cooling to 0° C. and neutralizaed with 3N hydrochloric acid to form a precipitate. Filtration and purification by recrystallization from a DMSO water solution obtained pure 4-amino-5-pyridyl-4H-1,2,4-triazole-thiol. Yield was 56.6%.

EXAMPLE 5: Methyl [4-amino-5-(3,4,5-trimethoxyphenyl-4H--1,2,4-triazol-3-yl]thio] acetate (27)

To a solution containing 20.0 mmol of 4-amino-5-(3,4,5-trimethoxyphenyl-4H-1,2,4-triazol-3-thiol in 50 ml of dry acetone was added 1.5 equivalent of anhydrous potassium carbonate. After stirring and cooling, 1.2 equivalent of methyl chloroacetate was added and refluxed for 10 hrs. It is filtered while hot and the filtrate was concentrated under reduced pressure. The precipitate was crystallized from ethanol. Yield was 71.3%°.

EXAMPLE 6: Ethyl 4[(4-amino-5-pyridyl-4H-1,2,4-triazol-3-yl) thiol] acetoacetate (46)

To 10.0 ml of ethanolic potassium hydroxide (10 mmol) solution was added 4-amino-5-pyridyl-4H-1,2,4-triazol-3-thiol (10.0 mmol). The mixture was stirred at 25° C. and 1.2 equivalent of methyl chloroacetate was added with continuous stirring for 5 hrs. Then 50 ml of water was poured into the mixture. After filtration and crystallization from ethanol, pure compound was obtained. Yield was 29.8%.

EXAMPLE 7: Ethyl 3-(p-chlorobenzyl)-7H-triazolo[3,4-b][1,3,4]-thiadiazin-6-yl] acetate (48)

To 4-amino-5-(p-chlorobenzyl) 4H-1,2,4-triazol 3-thiol (5.0 mmol) in 5 ml of anhydrous ethanol was added 1.2 equivalent of ethyl 4chloroacetoacetate. The mixture was stirred under reflux for 6 hr. After cooling at 0° C. overnight, a precipitate formed. The precipitate was recrystallized from ethanol. Yield was 63.5%.

EXAMPLE 8~16

The compounds 2-8,10,11 can be prepared in a manner analogous to thos described in example 3 and 4. The physical constants and spectral data are shown in Table I.

EXAMPLE 17~32

The compounds 12~26, 28 can be prepared in a manner analogous to that described in example 5. The physical constants and spectral data are shown in Table II.

EXAMPLE 33~50: 4,-5-disubstituter-4H-1,2,4-triazol-3-yl]thiol acetic acid

Methyl 4,5-Disubstituted-4H-1,2,4-triazol-3-yl]thiol acetate (10.0 mmol) was mixed with 30 ml of 1N aqueous sodium hydroxide solution and then refluxed for 4 hrs. The solution was neutralized with 3N hydrochloric acid to form a precipitate. After recrystallization from ethanol, the compounds 29~45 can be prepared. The physical constants and spectral data are shown in Table III.

EXAMPLE 51

The compound 47 can be prepared in a manner analogous to that described in example 6. The physical constants and spectral data are shown in Table IV.

EXAMPLE 52~53

The compound 49, 50 can be prepared in a manner analogous to that described in example 7. The physical constants and spectral data are shown in Table V.

EXAMPLE 54:
1-(p-chlorobenzyl)-4-benzyl-thiolsemicarbazide (53)

To a solution of p-chlorobenzyl-4-benzoic acid hydrazide (30.0 mmol) in 30 ml of ethanol was added 1.2 equivalent of ethyl isothiocyanate. The solution was mixed and refluxed for 4 hrs. After cooling to 0° C. a precipitate formed and crystallized from ethanol. Yield was 88.7%.

EXAMPLE 55~60

The compound 51, 52, 54~57 can be prepared in a manner analogous to that described in example 6. The physical constants and spectral data are shown in Table V.

TABLE 1

$$R_1 \underset{\underset{R_2}{|}}{\overset{N-N}{\diagup\diagdown}} SH$$

Figure 1:
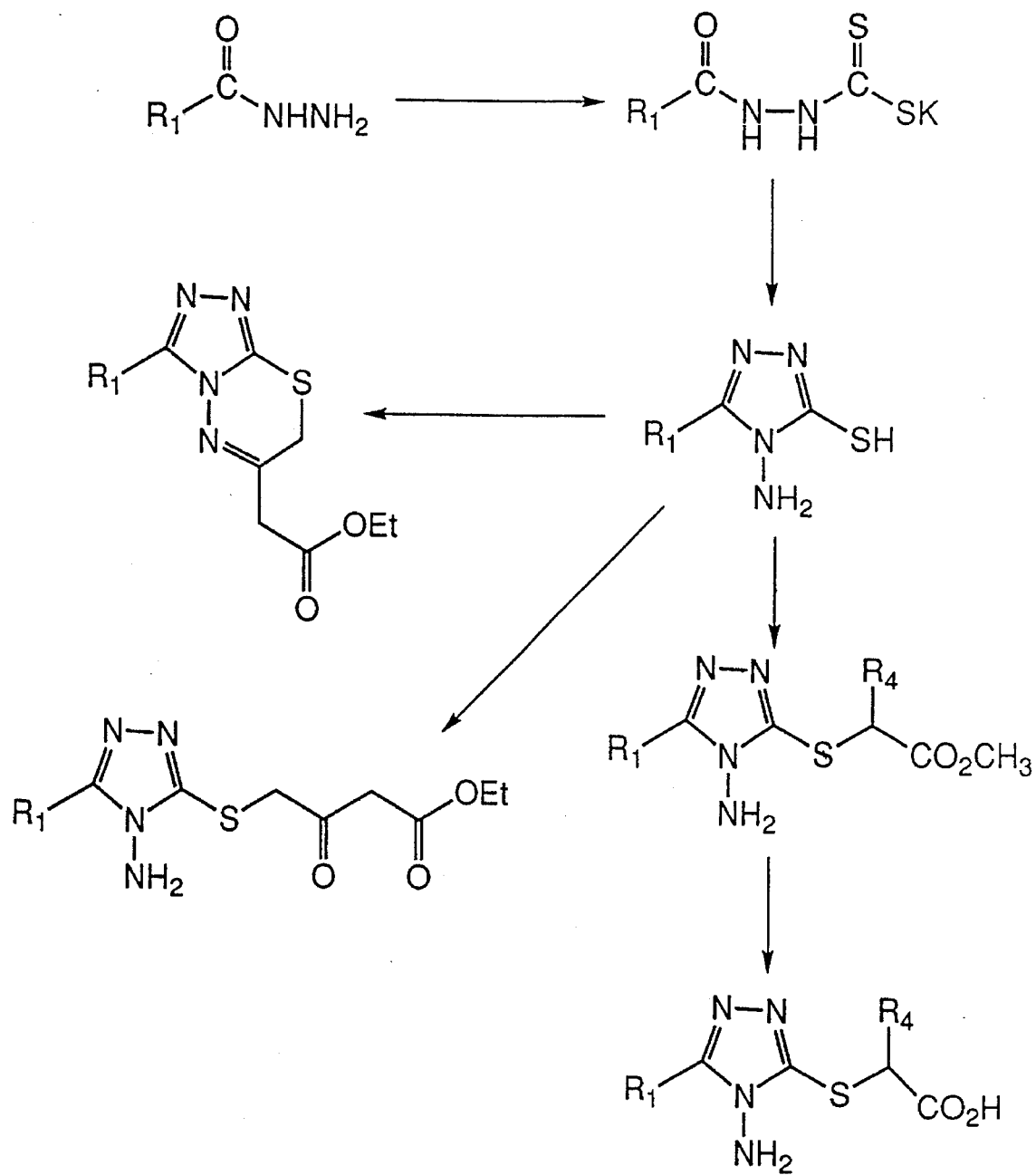
FIG. 1 represents a 4 step synthtic process for producing [4-amino-4H-1,2,4-triazol-3-yl]thio]acetate derivatives from aryl or hetero-aryl hydrazide starting materials.
Figure 2:
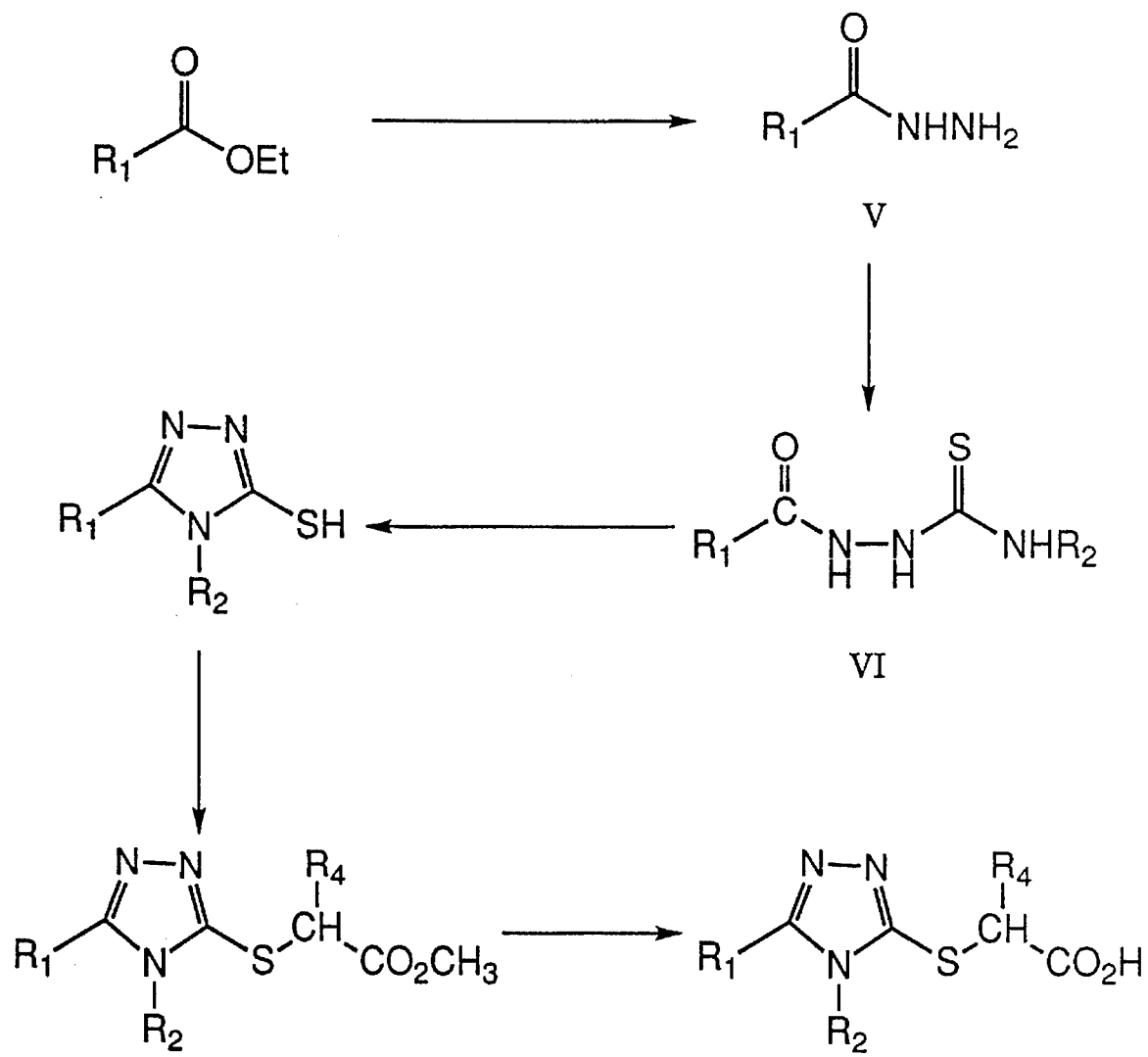
FIG. 2 represents a different 4 step synthetic synthesis for producing [4-amino-4H-1,2,4-triazol-3-yl]thio acetate derivatives from aryl or hetero-aryl-carboethoxy starting materials.

| Compound | $R_1$ | $R_2$ | Melting Point °C. | Yield % | MS(EI) m/z | NMR (DMSO-$d_6$) ppm |
|---|---|---|---|---|---|---|
| 1 | CH$_3$-C(=N-O-)- (isoxazolyl) | $C_6H_5$ | 201 | 94 | 285($M^+$), 185($M^+$-NNCSH), | 2.4(s, 3H, CH$_3$), 6.4(s, 1H, CH), 7.4–7.5(br, 5H, ArH) |
| 2 | CH$_3$-C(=N-O-)- (isoxazolyl) | $C_2H_5$ | 194 | 95 | 210($M^+$), 182($M^+$-C$_2$H$_4$), 109($M^+$-NC(S)NEt) | 1.3(t, 3H, CH$_3$), 2.5(s, 3H, CH$_3$), 4.3(q, 2H, CH$_2$), 6.7(s, 1H, CH) |
| 3 | 4-ClC$_6$H$_4$ | $C_6H_5$ | 266 | 87 | 287($M^+$), 214(ClC$_6$H$_4$CNPh$^+$), 137(ClC$_6$H$_4$CN$^+$) | 7.2–7.5(br, 9H, ArH), |
| 4 | 4-ClC$_6$H$_4$ | $C_2H_5$ | 204 | 92 | 239($M^+$), 2]]($M^+$-C$_2$H$_4$), 138(ClC$_6$H$_4$CNH$^+$) | 1.1(t, 3H, CH$_3$), 4.0(q, 2H, CH$_2$), 7.7(s, 4H, ArH) |
| 5 | 4-pyridyl | $C_6H_5$ | 282 | 90 | 254($M^+$), 104(NC$_5$H$_4$CN$^+$) | 7.2(d, 2H, ArH), 7.4–7.5(br, 5H, ArH), 8.5(d, 2H, ArH) |
| 6 | 4-pyridyl | $C_2H_5$ | 228 | 92 | 206($M^+$), 178($M^+$-C$_2$H$_4$), 105(NC$_5$H$_4$CNH$^+$) | 1.2(t, 3H, CH$_3$), 4.1(q, 2H, CH$_2$), 7.7(d, 2H, ArH), 8.8(d, 2H, ArH), |
| 7 | 3, 4, 5-(CH$_3$O)$_3$C$_6$H$_2$ | $C_6H_5$ | 209 | 89 | 343($M^+$), 193 ((CH$_3$O)$_3$C$_6$H$_2$CN$^+$) | 3.5(s, 6H, OCH$_3$), 3.6(s, 3H, OCH$_3$), 6.6(s, 2H, ArH), 7.3–7.5(br, 5H, ArH) |
| 8 | 4-ClC$_6$H$_4$ | NH$_2$ | 248 | 55 | 226($M^+$), 138($M^+$-NC(S)NNH$_2$) | 5.8(s, 2H, NH$_2$), 7.6(d, 2H, ArH), 8.0(d, 2H, ArH) |
| 9 | 4-pyridyl | NH$_2$ | 248 | 57 | 193($M^+$), 105($M^+$-NC(S)NNH$_2$) | 5.9(s, 2H, NH$_2$), 8.0(d, 2H, ArH), 8.7(d, 2H, ArH) |
| 10 | 3, 4, 5-(CH$_3$O)$_3$C$_6$H$_2$ | NH$_2$ | 221 | 57 | 282($M^+$), 194($M^+$-NC(S)NNH$_2$) | 3.7(s, 3H, OCH$_3$), 3.8(s, 6H, OCH$_3$), 5.8(s, 2H, NH$_2$), 7.3(s, 2H, ArH) |
| 11 | $C_6H_6$ | NH$_2$ | 206 | 59 | 192($M^+$), 104($M^+$-NC(S)NNH$_2$) | 5.8(s, 2H, NH$_2$), 7.4–8(br, 5H, ArH) |

TABLE 2

$$\underset{R_2}{\underset{|}{R_1-}}\overset{N-N}{\underset{}{\diagup\hspace{-0.2em}\diagdown}}-S-\underset{R_4}{\underset{|}{CH}}-CO_2Me$$

| Compound | R₁ | R₂ | R₄ | Melting Point °C. | Yield % | MS(EI) m/z | NMR(DMSO-d₆) ppm |
|---|---|---|---|---|---|---|---|
| 12 | CH₃-C(=)-isoxazole (5-methylisoxazol-3-yl) | C₆H₅ | H | 133 | 51 | 330(M⁺), 298(M⁺-CH₃OH), 271(M⁺-CO₂CH₃), 257(M⁺-CH₂CO₂CH₃) | 2.4(s, 3H, CH₃), 3.7(s, 3H, CH₃), 4.1(s, 2H, CH₂), 6.5(s, 1H, CH), 7.3–7.6(br, 5H, ArH) |
| 13 | 5-methylisoxazol-3-yl | C₆H₅ | CH₃ | 94 | 44 | 344(M⁺), 313(M⁺-CH₃O), 285(M⁺-CO₂CH₃), 258(M⁺-CH₂CHCO₂CH₃) | 1.5(d, 3H, CH₃), 2.4(s, 3H, CH₃), 3.6(s, 3H, CH₃), 4.4(q, 1H, CH) 6.5(s, 1H, CH), 7.4–7.6(br, 5H, ArH) |
| 14 | 5-methylisoxazol-3-yl | C₂H₅ | H | 105 | 54 | 282(M⁺), 250(M⁺-CH₂OH), 223(M⁺-CO₂CH₃), 209(M⁺-CH₂CO₂CH₃) | 1.3(t, 3H, CH₃), 2.5(s, 1H, CH₃), 3.7(s, 3H, CH₃), 4.2(q, 2H, CH₂) 4.3(q, 2H, CH₂), 6.8(s, 1H, CH) |
| 15 | 5-methylisoxazol-3-yl | C₂H₅ | CH₃ | [a] | 49 | 296(M⁺), 264(M⁺-CH₃OH), 209(M⁺-CH₂CHCOOCH₃) | 1.3(t, 3H, CH₃), 1.5(d, 3H, CH₃), 2.5(s, 3H, CH₃), 3.6(s, 3H, CH₃), 4.3(q, 3H, CH and CH₂), 6.8(s, 1H, CH) |
| 16 | 4-ClC₆H₄ | C₆H₅ | H | 157 | 42 | 359(M⁺), 327(M⁺-CH₃OH), 300(M⁺-COOCH₃), 286(M⁺-CH₂COOCH₃) | 3.6(s, 3H, CH₃), 4.1(s, 2H, CH₂), 7.4–7.6(br, 9H, ArH) |
| 17 | 4-ClC₆H₄ | C₆H₅ | CH₃ | 82 | 11 | 373(M⁺), 342(M⁺-CH₃O), 314(M⁺-COOCH₃), 287(M⁺-CH₂CHCOOCH₃) | 1.5(d, 3H, CH₃), 3.6(s, 3H, CH₃), 4.3(q, 1H, CH), 7.3–7.5(br, 9H, ArH) |
| 18 | 4-ClC₆H₄ | C₂H₅ | H | 89 | 52 | 311(M⁺), 280(M⁺-CH₃O), 252(M⁺-COOCH₃), 238(M⁺-CH₂COOCH₃) | 1.2(t, 3H, CH₃), 3.7(s, 3H, CH₃), 4.0(q, 2H, CH₂), 4.2(s, 2H, CH₂), 7.6(s, 4H, ArH) |
| 19 | 4-ClC₆H₄ | C₂H₅ | CH₃ | 87 | 50 | 325(M⁺), 294(M⁺-CH₃O), 266(M⁺-COOCH₃), 238(M⁺-CH₃CHCOOCH₃) | 1.2(t, 3H, CH₃), 1.6(d, 3H, CH₃), 3.6(s, 3H, CH₃), 4.0(q, 2H, CH₂), 4.3(q, 1H, CH), 7.7(s, 4H, ArH) |
| 20 | 4-pyridyl | C₆H₅ | H | 153 | 38 | 326(M⁺), 294(M⁺-CH₃OH), 267(M⁺-COOCH₃), 253(M⁺-CH₂COOCH₃) | 3.7(s, 3H, CH₃), 4.1(s, 2H, CH₂), 7.3(d, 2H, ArH), 7.5–7.6(br, 5H, ArH), 8.5(d, 2H, ArH) |
| 21 | 4-pyridyl | C₆H₅ | CH₃ | 79 | 20 | 340(M⁺), 309(M⁺-CH₂O), 281(M⁺-COOCH₃), 254(M⁺-CH₂CHCOOCH₃) | 1.5(d, 3H, CH₃), 3.6(s, 3H, CH₃), 4.3(q, 1H, CH), 7.5–7.6(br, 5H, ArH), 7.4(d, 2H, ArH), 8.5(d, 2H, ArH) |
| 22 | 4-pyridyl | C₂H₅ | H | 78 | 50 | 278(M⁺), 246(M⁺-CH₂OH), 219(M⁺-COOCH₃), 205(M⁺-CH₂COOCH₃) | 1.3(t, 3H, CH₃), 3.7(s, 3H, CH₃), 4.1(q, 2H, CH₂), 4.2(s, 2H, CH₂), 7.7(d, 2H, ArH), 8.7(d, 2H, ArH) |
| 23 | 4-pyridyl | C₂H₅ | CH₃ | [a] | 48 | 292(M⁺), 260(M⁺-CH₃OH), 233(M⁺-COOCH₃), 205(M⁺-CH₃CHCOOCH₃) | 1.3(t, 3H, CH₃), 1.6(d, 3H, CH₃), 3.7(s, 3H, CH₃), 4.1(q, 2H, CH₂), 4.3(q, 1H, CH), 7.7(d, 2H, ArH), 8.8(d, 2H, ArH) |
| 24 | 3, 4, 5-(CH₃O)₃C₆H₂ | C₆H₅ | CH₃ | 113 | 72 | 429(M⁺), 398(M⁺-CH₃O), 370(M⁺-COOCH₃), 343(M⁺-CH₂CHCOOCH₃) | 1.5(d, 2H, CH₃), 3.5(s, 6H, OCH₃), 3.6(s, 3H, OCH₃), 3.7(s, 3H, CH₃), 4.3(q, 1H, CH), 6.6(s, 2H, ArH), 7.4–7.6(br, 5H, ArH) |
| 25 | 4-ClC₆H₄ | NH₂ | H | 205 | 69 | 298(M⁺), 266(M⁺-CH₂OH), 239(M⁺-CO₂CH₃) | 3.7(s, 3H, CH₃), 4.1(s, 2H, CH₂), 6.2(s, 2H, NH₂), 7.6(d, 2H, ArH), 8.0(d, 2H, ArH) |
| 26 | 4-pyridyl | NH₂ | H | 194 | 45 | 265(M⁺), 233(M⁺-CH₂OH), 206(M⁺-CO₂CH₃) | 3.7(s, 3H, CH₃), 4.1(s, 2H, CH₂), 6.3(s, 2H, NH₂), 8.0(d, 2H, ArH), 8.7(d, 2H, ArH) |
| 27 | 3, 4, 5-(CH₃O)₃C₆H₂ | NH₂ | H | 136 | 71 | 354(M⁺), 323(M⁺-CH₃O), 295(M⁺-CO₂CH₃), | 3.66(s, 3H, CH₃), 3.68(s, 3H, OCH₃), 3.7(s, 6H, OCH₃), |

TABLE 2-continued $$R_1 \underset{\underset{R_2}{|}}{\overset{N-N}{\underset{N}{\diagup\!\!\!\diagdown}}} S\underset{\underset{R_4}{|}}{\overset{}{CH}}CO_2Me$$

| Compound | $R_1$ | $R_2$ | $R_4$ | Melting Point °C. | Yield % | MS(EI) m/z | NMR(DMSO-$d_6$) ppm |
|---|---|---|---|---|---|---|---|
| 28 | $C_6H_5$ | $NH_2$ | H | 179 | 96 | 281($M^+$-$CH_2CO_2CH_3$) 264($M^+$), 232($M^+$-$CH_3OH$), 205($M^+$-$CO_2CH_3$) | 4.1(s, 2H, $CH_2$), 6.2(s, 2H, $NH_2$), 7.2(s, 2H, ArH) 3.7(s, 3H, $CH_3$), 4.1(s, 2H, $CH_2$), 6.2(s, 2H, $NH_2$), 7.4–8.0(br, 5H, ArH) |

TABLE 3

$$R_1 \underset{\underset{R_2}{|}}{\overset{N-N}{\underset{N}{\diagup\!\!\!\diagdown}}} S\underset{\underset{R_4}{|}}{\overset{}{CH}}CO_2H$$

| Compound | $R_1$ | $R_2$ | $R_4$ | Melting Point °C. | Yield % | IR cm$^{-1}$ | MS(EI) m/z | NMR(DMSO-$d_6$) ppm | Element Analysis Calcd./Found C | H | N |
|---|---|---|---|---|---|---|---|---|---|---|---|
| 29 | 4-ClC$_6$H$_4$ | $C_2H_5$ | H | 218 | 77 | 3300–2300 (COOH) 1731 (C=O) | 297($M^+$), 252($M^+$-COOH), 238 ($M^+$-$CH_2CO_2$) | 1.2(t, 3H, $CH_3$), 4.0(q, 2H, $CH_2$), 4.1(s, 2H, $CH_2$), 7.6(s, 4H, ArH) | 48.03 48.40 | 4.04 4.06 | 14.03 14.11 |
| 30 | 4-ClC$_6$H$_4$ | $C_2H_5$ | $CH_3$ | 182 | 74 | 3200-2300 (COOH) 1745 (C=O) | 311($M^+$), 293($M^+$-$H_2O$), 267($M^+$-$CO_2$), | 1.2(t, 3H, $CH_3$), 1.6(d, 3H, $CH_3$), 4.0(q, 2H, $CH_2$), 4.2(q, 1H, CH), 7.7(s, 4H, ArH) | 50.08 50.40 | 4.52 4.46 | 13.47 13.47 |
| 31 | 4-pyridyl | $C_6H_5$ | H | 239 | 40 | 3200-2300 (COOH) 1704 (C=O) | 312($M^+$), 294($M^+$-$H_2O$), 268($M^+$-$CO_2$), 253($M^+$-$CH_2CO_2H$) | 4.1(s, 2H, $CH_2$), 7.3(d, 2H, ArH), 7.5–7.6(br, 5H, ArH), 8.5(d, 2H, ArH) | 57.68 57.60 | 3.87 3.84 | 17.94 17.93 |
| 32 | 4-pyridyl | $C_6H_5$ | $CH_3$ | 258 | 22 | 3200-2300 (COOH) 1712 (C=O) | 326($M^+$), 308($M^+$-$H_2O$), 282($M^+$-$CO_2$), | 1.5(d, 3H, $CH_3$), 4.3(q, 1H, CH), 7.3(d, 2H, ArH), 7.4–7.6(br, 5H, ArH), 8.6(d, 2H, ArH) | 58.88 58.90 | 4.32 4.30 | 17.16 17.15 |
| 33 | 4-pyridyl | $C_2H_5$ | H | 209 | 35 | 3200-2300 (COOH) 1711 (C=O) | 264($M^+$), 220(($M^+$-$CO_2$), 205($M^+$-$CH_2CO_2H$) | 1.3(t, 3H, $CH_3$), 4.1(s, 2H, $CH_2$), 4.0(q, 2H, $CH_2$), 4.0(q, 2H, $CH_2$), 7.7(d, 2H, ArH), 8.8(d, 2H, ArH) | 49.99 49.91 | 4.58 4.57 | 21.20 21.02 |
| 34 | 4-pyridyl | $C_2H_5$ | $CH_3$ | 171 | 20 | 3200-2300 (COOH) 1712 (C=O) | 278($M^+$), 234($M^+$-$CO_2$) | 1.3(t, 3H, $CH_3$), 1.5(3, 3H, $CH_3$), 4.1(q, 2H, $CH_2$), 4.2(q, 1H, CH), 7.7(d, 2H, ArH), 8.7(d, 2H, ArH) | 51.76 51.81 | 5.13 5.11 | 20.12 20.11 |
| 35 | 3, 4, 5-(HO)$_3$C$_6$H$_2$ | $C_6H_5$ | $CH_3$ | 240 | 68 | 3200-2300 (COOH) 1711 (C=O) | 373($M^+$), 356($M^+$-CH), 329($M^+$-$CO_2$) | 1.5(d, 3H, $CH_3$), 4.2(q, 1H, CH), 6.3(s, 2H, ArH), 7.5–7.6(br, 5H, ArH), 8.5(s, 1H, OH), 9.0(s, 2H, OH) | 53.48 53.95 | 3.65 3.90 | 11.15 11.69 |
| 36 | 4-ClC$_6$H$_4$ | $NH_2$ | H | 203 | 78 | 3200-2300 (COOH) 1710 | 284($M^+$), 266($M^+$-$H_2O$), 240($M^+$-$CO_2$) | 4.0(s, 2H, $CH_2$), 6.2(s, 2H, $NH_2$), 7.6(d, 2H, ArH), | 42.18 43.16 | 3.19 3.09 | 19.67 19.62 |

TABLE 3-continued $$\underset{R_2}{\overset{N-N}{R_1\diagdown\underset{|}{N}\diagup}}S\underset{R_4}{\overset{|}{CH}}CO_2H$$

| Compound | R₁ | R₂ | R₄ | Melting Point °C. | Yield % | IR cm⁻¹ | MS(EI) m/z | NMR(DMSO-d₆) ppm | Element Analysis Calcd./Found C | H | N |
|---|---|---|---|---|---|---|---|---|---|---|---|
| | | | | | | (C=O) | | 8.0(d, 2H, ArH) | | | |
| 37 | 4-pyridyl | NH₂ | H | 263 | 44 | 3200-2300 (COOH) 1712 (C=O) | 251(M⁺), 233(M⁺-H₂O), 207(M⁺-CO₂) | 4.1(s, 2H, CH₂), 6.3(s, 2H, NH₂), 8.0)d, 2H, ArH), 8.7(d, 2H, ArH) | 43.02 / 43.08 | 3.61 / 3.58 | 27.87 / 27.85 |
| 38 | 3,4,5-(CH₃O)₃C₆H₂ | NH₂ | H | 228 | 71 | 3200-2300 (COOH) 1713 (C=O) | 340(M⁺), 322(M⁺-H₂O), 296(M⁺-CO₂) | 3.7(s, 3H, OCH₃), 3.8(s, 6H, OCH₃), 4.0(s2H, CH₂), 6.1(s, 2H, NH₂), 7.2(s, 2H, ArH) | 45.88 / 45.99 | 4.74 / 4.56 | 16.46 / 16.42 |
| 39 | C₆H₅ | NH₂ | H | 187 | 63 | 3200-2300 (COOH) 1713 (C=O) | 250(M⁺), 232(M⁺-H₂O), 206(M⁺-CO₂) | 4.0(s, 2H, CH₂), 6.2(s, 2H, NH₂), 7.4-8.0(br, 5H, ArH) | 47.99 / 47.73 | 4.03 / 4.05 | 22.38 / 22.39 |
| 40 | 3-methyl-isoxazol-5-yl | C₆H₅ | H | 227 | 74 | 3300-2300 (COOH) 1712 (C=O) | 316(M⁺), 299(M⁺-OH), 272(M⁺-CO₂), 257(M⁺-CH₂CO₂H) | 2.4(s, 3H, CH₃), 4.1(s, 2H, CH₂), 6.5(s, 1H, CH), 7.4-7.6(br, 5H, ArH) | 53.15 / 52.98 | 3.82 / 3.76 | 17.71 / 17.74 |
| 41 | 3-methyl-isoxazol-5-yl | C₆H₅ | CH₃ | 182 | 71 | 3300-2300 (COOH) 1746 (C=O) | 330(M⁺), 286(M⁺-CO₂) | 1.5(d, 3H, CH₃), 2.4(s, 3H, CH₃), 4.3(q, 1H, CH) 6.5(s, 1H, CH), 7.4-7.6(br, 5H, ArH) | 54.53 / 54.42 | 4.27 / 4.23 | 16.96 / 16.98 |
| 42 | 3-methyl-isoxazol-5-yl | C₂H₅ | H | 163 | 61 | 3300-2300 (COOH) 1731 (C=O) | 268(M⁺), 251(M⁺-OH), 224(M⁺-CO₂), 209(M⁺-CH₂CO₂H) | 1.3(t, 3H, CH₃), 2.5(s, 1H, CH₃), 4.1(s, 2H, CH₂) 4.3(q, 2H, CH₂) 6.8(s, 1H, CH) | 44.76 / 44.57 | 4.50 / 4.47 | 20.88 / 20.94 |
| 43 | 3-methyl-isoxazol-5-yl | C₂H₅ | CH₃ | 105 | 40 | 3300-2300 (COOH) 1731 (C=O) | 282(M⁺), 238(M⁺-CO₂) | 1.3(t, 3H, CH₃), 1.5(d, 3H, CH₃), 2.5(s, 3H, CH₃), 4.3(q, 3H and CH₂) 6.8(s, 1H, CH) | 46.80 / 46.60 | 5.00 / 4.91 | 19.85 / 19.84 |
| 44 | 4-ClC₆H₄ | C₆H₅ | H | 233 | 78 | 3300-2300 (COOH) 1745 (C=O) | 345(M⁺), 301(M⁺-CO₂), 287 (M⁺-CH₂CO₂H) | 4.0(s, 2H, CH₂), 7.3-7.5(br, 9H, ArH) | 55.57 / 55.50 | 3.50 / 3.41 | 12.15 / 12.14 |
| 45 | 4-ClC₆H₄ | C₆H₅ | CH₃ | 195 | 75 | 3300-2300 (COOH) 1737 (C=O) | 359(M⁺), 341(M⁺-H₂O), 315(M⁺-CO₂), | 1.5(d, 3H, CH₃), 4.3(q, 1H, CH), 7.3-7.6(br, 9H, ArH) | 56.74 / 56.68 | 3.92 / 3.81 | 11.67 / 11.67 |

TABLE 4

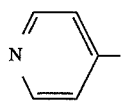

| Compound | R₁ | Melting Point °C. | Yield % | IR cm⁻¹ | MS(EI) m/z | NMR(DMSO-$d_6$) ppm | Element Analysis Calcd./Found C | H | N |
|---|---|---|---|---|---|---|---|---|---|
| 46 | 4-pyridyl | 154 | 30 | 3462, 3190 (NH) 1745 (C=O) | 303(M⁺-H₂O), 257(M⁺-H₂O-EtOH) | 1.2(t, 3H, CH₃), 2.8(s, 2H, CH₂), 4.1(q, 2H, CH₂), 6.5(s, 1H, CH), 7.1(s, 2H, NH₂), 8.0(d, 2H, ArH), 8.7(d, 2H, ArH) | 48.58 45.17 | 4.70 4.39 | 21.79 22.19 |
| 47 | 3, 4, 5-(CH₃O)₃C₆H₂ | 142 | 74 | 3462, 3133 (NH) 1707 (C=O) | 392(M⁺-H₂O), | 1.2(t, 3H, CH₃) 2.8(s, 2H, CH₂), 3.7(s, 3H, OCH₃), 3.8(s, 6H, OCH₃), 4.1(q, 2H, CH₂), 6.5(s, 1H, CH), 7.1(s, 2H, NH₂), 7.4(d, 2H, ArH) | 49.74 47.65 | 5.40 5.40 | 13.65 13.04 |

TABLE 5

| Compound | R₁ | Melting Point °C. | Yield % | IR cm⁻¹ | MS(EI) m/z | NMR(DMSO-$d_6$) ppm | Element Analysis Calcd./Found C | H | N |
|---|---|---|---|---|---|---|---|---|---|
| 48 | p-ClC₆H₄ | 148 | 64 | 1726(C=O) 1190(C—O) | 336(M⁺), 290(M⁺-EtOH) | 1.2(t, 3H, CH₃), 3.8(s, 2H, CH₂), 3.9(s, 2H, CH₂), 4.1(q, 2H, CH₂), 7.6(d, 2H, ArH), 7.9(d, 2H, ArH) | 49.93 49.93 | 3.89 3.87 | 16.64 16.68 |
| 49 | 3, 4, 5-(CH₃O)₃C₆H₂ | 120 | 69 | 1722(C=O) 1193(C—O) | 392(M⁺), 346(M⁺-EtOH) | 1.2(t, 3H, CH₃), 3.7(s, 3H, OCH₃), 3.84(s, 6H, OCH₃), 3.86(s, 2H, CH₂), 3.9(s, 2H, CH₂), 4.1(q, 2H, CH₂), 7.2(s, 2H, ArH), | 51.98 51.76 | 5.14 5.18 | 14.28 14.24 |
| 50 | C₆H₅ | 163 | 56 | 1722(C=O) 1192(C—O) | 302(M⁺), 256(M⁺-EtOH) | 1.3(t, 3H, CH₃), 3.6(s, 2H, CH₂), 3.7(s, 2H, CH₂), 4.2(q, 2H, CH₂), 7.4–7.9(m, 5H, ArH) | 55.61 55.17 | 4.66 4.58 | 18.53 18.57 |

TABLE 6

$$R-\overset{O}{\underset{\|}{C}}-NH-NH-\overset{S}{\underset{\|}{C}}-NHR_2$$

| Compound | R₁ | R₂ | Melting Point °C. | Yield % | Ms(EI) m/z | NMR(DMSO-d₆) ppm |
|---|---|---|---|---|---|---|
| 51 | (5-methyl-isoxazol-3-yl) CH₃-...O-N | C₆H₅ | 98 | 59 | 276(M⁺), 141(M⁺-C(S)NPh), 136(C(S)NHPh⁺) | 2.1(s, 3H, CH₃), 6.6(s, 1H, CH), 7.3–7.5(br, 5H, ArH), 9.7(s, 1H, NH), 9.8(s, 1H, NH), 10.6(s, 1H, NH) |
| 52 | (5-methyl-isoxazol-3-yl) CH₃-...O-N | C₂H₅ | 167 | 72 | 228(M⁺), 141(M⁺-C(S)NEt), 110(M⁺-N₂H₂C(S)NHEt) | 1.1(t, 3H, CH₃), 2.5(s, 3H, CH), 3.6(q, 2H, CH₂), 6.6(s, 1H, CH), 8.1(s, 1H, NH), 9.3(s, 1H, NH), 10.4(s, 1H, NH) |
| 53 | 4-ClC₆H₄ | C₆H₅ | 180 | 89 | 305(M⁺), 212(M⁺-PhNH), 170(M⁺-SCNPh), 139(ClC₆H₄C(O)⁺) | 7.2–8.0(br, 9H, ArH), 9.6(s, 1H, NH), 9.7(s, 1H, NH), 10.5(s, 1H, NH) |
| 54 | 4-ClC₆H₄ | C₂H₅ | 203 | 98 | 257(M⁺), 170(M⁺-SCNEt), 139(ClC₆H₄C(O)⁺) | 1.1(t, 3H, CH₃), 3.45(q, 2H, CH₂), 7.4–7.9(br, 4H, ArH), 8.0(s, 1H, NH), 9.2(s, 1H, NH), 10.4(s, 1H, NH) |
| 55 | pyridyl | C₆H₅ | 185 | 53 | 272(M⁺), 179(M⁺-PhNH₂), 135(SCNPh⁺), 106(NC₅H₄C(O)⁺) | 7.1–7.4(br, 5H, ArH), 7.7(d, 2H, ArH), 8.7(d, 2H, ArH), 9.8(s, 1H, NH), 9.9(s, 1H, NH), 10.8(s, 1H, NH) |
| 56 | pyridyl | C₂H₅ | 215 | 85 | 224(M⁺), 137(M⁺-SCNEt), 106(NC₅H₄C(O)⁺) | 1.1(t, 3H, CH₃), 3.4(q, 2H, CH₂), 7.7(d, 2H, ArH), 8.8(d, 2H, ArH), 8.1(s, 1H, NH), 9.3(s, 1H, NH), 10.6(s, 1H, NH) |
| 57 | 3,4,5-(CH₃O)₃C₆H₂ | C₆H₅ | 194 | 94 | 361(M⁺), 268(M⁺-PhNH₂), 195((CH₃O)₃C₆H₂C(O)⁺) | 3.7(s, 3H, OCH₃), 3.8(s, 6H, OCH₃), 7.3(s, 2H, ArH), 7.2–7.5(br, 5H, ArH), 9.6(s, 1H, NH), 9.7(s, 1H, NH), 10.5(s, 1H, NH) |

TABLE 7

| Compound | Concentration (mg/Kg) | Antiinflammatory Percentage |
|---|---|---|
| 40 | 32 | — |
| 41 | 32 | 9.30 |
| 42 | 32 | −4.65 |
| 43 | 32 | 46.51 |
| 44 | 32 | 39.53 |
| 45 | 32 | 23.26 |
| 29 | 32 | −46.51 |
| 30 | 32 | 11.63 |
| 31 | 32 | −60.47 |
| 32 | 32 | −23.26 |
| 33 | 32 | −60.47 |
| 34 | 32 | −18.6 |
| 35 | 32 | −97.67 |
| 36 | 32 | 32.56 |
| 37 | 32 | 11.63 |
| 38 | 32 | −18.6 |
| 39 | 32 | 20.93 |
| 48 | 32 | 55.81 |
| 49 | 32 | 44.19 |
| 50 | 32 | −48.84 |
| 46 | 32 | 2.33 |
| Phenylbutazone | 32 | 9.30 |
| dexamethasone | 32 | 53.49 |
|  | 32 | 65.12 |

What I claim is:

1. A compound of formula III

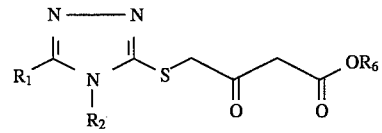

wherein R₁ represents a phenyl group which is optionally substituted by one or more halogens, or methoxy group, or $C_{1-4}$ alkyl, or represents a pyridyl group which is optionally substituted by one or more halogens, or methoxyl group, or $C_{1-4}$ alkyl, or represents a 3-isoxazole group which is optionally substituted by one or more halogens, or methoxyl group, or $C_{1-4}$ alkyl, R₂ represents a $C_{1-4}$ alkyl group, or an amino group, or represents a phenyl group which is optionally substituted by one or more halogens, or methoxyl group, or $C_{1-4}$ alkyl, R₆ represents a hydrogen, or $C_{1-4}$ alkyl group, or salts thereof.

2. A compound of claim 1 wherein R₁ represents a phenyl group which is optionally substituted by one to three halogens, or methoxy group, or $C_{1-4}$ alkyl, or represents a pyridyl group which is optionally substituted by one to three halogens, or methoxyl group, or $C_{1-4}$ alkyl, or represents a 3-isoxazole group which is optionally substituted by one to three halogens, or methoxyl group, or $C_{1-4}$ alkly, $R_2$ represents a phenyl group which is optionally substituted by one to three halogens, or methoxyl group, or $C_{1-4}$ alkyl.

3. A compound of claim 1 wherein $R_1$ represents a 3-isoxazole, phenyl, pyridyl, or represents a phenyl group which is optionally substituted by one to three chlorines, or methoxyl group, or methyl, or represents a 3-isoxazole group which is optionally substituted by one to three chlorines, or methoxyl group, or methyl, $R_2$ represents a $C_{1-4}$ alkyl group, phenyl, or an amino group, or represents a phenyl group which is optionally substituted by one to three chlorines, or methoxyl group, or $C_{1-4}$ alkyl, $R_6$ represents a hydrogen, or $C_{1-4}$ alkyl group.

* * * * *